(12) United States Patent
Tsuchida et al.

(10) Patent No.: US 8,080,695 B2
(45) Date of Patent: Dec. 20, 2011

(54) METHOD OF SYNTHESIZING HIGHER-MOLECULAR ALCOHOL

(75) Inventors: Takashi Tsuchida, Tokyo (JP); Shuji Sakuma, Tokyo (JP)

(73) Assignee: Kabushiki Kaisha Sangi, Tokyo (JP)

( * ) Notice: Subject to any disclaimer, the term of this patent is extended or adjusted under 35 U.S.C. 154(b) by 0 days.

(21) Appl. No.: 11/757,588

(22) Filed: Jun. 4, 2007

(65) Prior Publication Data

US 2007/0255079 A1 Nov. 1, 2007

Related U.S. Application Data

(63) Continuation-in-part of application No. PCT/JP2005/022217, filed on Dec. 2, 2005.

(30) Foreign Application Priority Data

Dec. 3, 2004 (JP) ................................. 2004-351307

(51) Int. Cl.
*C07C 31/02* (2006.01)
(52) U.S. Cl. .................................... 568/902; 568/902.2
(58) Field of Classification Search .................. 568/902, 568/902.2, 869
See application file for complete search history.

(56) References Cited

U.S. PATENT DOCUMENTS 2,645,667 A * 7/1953 Burgoyne ..................... 568/715
6,323,383 B1 * 11/2001 Tsuchida et al. ............. 585/601

FOREIGN PATENT DOCUMENTS

EP 1 052 234 A1 11/2000
WO WO 99/38822 8/1999

OTHER PUBLICATIONS

Mysov, V.M. et al. (2005). "Synthesis Gas Conversion Into Hydrocarbons (Gasoline Range) Over Bifunctional Zeolite-Containing Catalyst: Experimental Study and Mathematical Modelling," *Chemical Engineering Journal* 107:63-71.
Ndou, A.S. et al. (2003). "Dimerisation of Ethanol to Butanol Over Solid-Base Catalysts," *Applied Catalysis A: General* 251:337-345.
Yang, C. et al. (1993). "Bimolecular Condensation of Ethanol to 1-Butanol Catalyzed by Alkali Cation Zeolites," *Journal of Catalysis* 142:37-44.

* cited by examiner

*Primary Examiner* — Sikarl Witherspoon
(74) *Attorney, Agent, or Firm* — Hodgson Russ LLP

(57) ABSTRACT

The present invention provides a production method with which high molecular alcohols having an even number of carbon atoms such as 1-butanol, hexanol, octanol and decanol, and a mixture of these are efficiently collected through clean processes with the use of ethanol as a raw material. High molecular alcohols are produced from ethanol by using calcium phosphate-based compounds such as hydroxyapatite $Ca_{10}(PO_4)_6(OH)_2$, tricalcium phosphate $Ca_3(PO_4)_2$, calcium monohydrogen phosphate $CaHPO_4.(0~2)H_2O$, calcium diphosphate $Ca_2P_2O_7$, octacalcium phosphate $Ca_8H_2(PO_4)_6.5H_2O$, tetracalcium phosphate $Ca_4(PO_4)_2O$ or amorphous calcium phosphate $Ca_3(PO_4)_2 \cdot nH_2O$ as a catalyst, using ethanol as a starting material, and setting a contact time at 0.4 second or longer.

19 Claims, 2 Drawing Sheets

METHOD OF SYNTHESIZING HIGHER-MOLECULAR ALCOHOL

INCORPORATION BY REFERENCE

This application is a continuation-in-part application of international patent application Serial No. PCT/JP2005/022217 filed Dec. 2, 2005, which claims priority to Japanese patent application Serial No. JP 2004-351307 filed Dec. 3, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a method for producing high molecular alcohols from ethanol with the use of calcium phosphate-based catalysts.

BACKGROUND OF THE INVENTION

High molecular alcohols such as butanol ($C_4H_9OH$), hexanol ($C_6H_{13}OH$), octanol ($C_8H_{17}OH$), and decanol ($C_{10}H_{21}OH$) are currently synthesized by the oxo method using propylene obtained from petroleum as a raw material. However, as crude oil prices exceeded 50 dollars/barrel in 2004, and the soaring prices of propylene as a raw material led to the rising production cost of high molecular alcohols, the result is a worsened profitability.

The oxo method necessitates the use of deadly carbon monoxide as a raw material in addition to propylene, and the method comprises a complicated, high-pressure reaction which contributes to the rising production costs. Furthermore, the oxo method is unpreferable in view of environmental conservation. As an example, butanol synthesis reactions involve the generation of 2 moles of carbon dioxide as a side product per 1 mole of butanol as shown in reaction (1), and carbon dioxide is a well-known global warming substance.

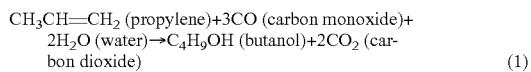

$$CH_3CH=CH_2 \text{ (propylene)}+3CO \text{ (carbon monoxide)}+ 2H_2O \text{ (water)} \rightarrow C_4H_9OH \text{ (butanol)}+2CO_2 \text{ (carbon dioxide)} \quad (1)$$

Relating to methods for synthesizing 1-butanol from ethanol, both MgO catalysts ("Dimerisation of ethanol to butanol over solid-base catalysts" A. S. Ndou, N. plint, N. J. Coville, Applied catalysis A: General, 251, p. 337-345 (2003)) and zeolite (ZSM-5) catalysts on which alkali metals are supported ("Bimolecular Condensation of Ethanol to 1-Butanol Catalyzed by Alkali Cation Zeolites" C. Yang, Z. Meng, J. of Catalysis, 142, p. 37-44 (1993)) have been used. However, they are not industrially suitable because of their low selectivity.

International Publication No. WO 99/38822 relates to a method for synthesizing 1-butanol with the use of calcium phosphate-based catalysts, although this synthesis method features disadvantages which are associated with the high reaction temperature (as high as 350 to 450° C.) that is involved. For instance, the selectivity of 1-butanol is low; the catalyst regeneration treatment has to be repeated frequently because of the rapid degradation of catalytic property; the durability of devices is decreased; and the fuel cost required for maintaining the reaction temperature is increased.

Thus, there is a clear need for an efficient and clean method of producing high-molecular alcohols from ethanol.

SUMMARY OF THE INVENTION

The object of the present invention is to provide a production method with which high molecular alcohols having an even number of carbon atoms such as 1-butanol, hexanol, octanol, and decanol, and a mixture of these, are efficiently collected through clean processes, with the use of ethanol as a raw material.

Ethanol, which is the starting material of the process of the present application, is currently synthesized through the conversion of sugars obtained from sugarcanes, beets, etc., by a fermentation method. Recently, a technique for synthesizing ethanol from biomass, agricultural and forestry residues, has been established, and a striking increase in the production of ethanol can be expected in the future. As a result, the production cost of ethanol is expected to lower to the level comparable to that of crude oil. In fact, it is said that the production cost of ethanol is about 10 yen/l in Brazil, an advanced country in terms of ethanol, and this is comparable to or less expensive than the international crude oil prices. Therefore, it is considered that the process of the present application can obtain high molecular alcohols which are less expensive than those obtained through the oxo method.

In the method for synthesizing high molecular alcohols according to the present application, the raw material may be only ethanol, and the reaction may proceed easily at normal pressure. Further, the side product of the synthesis reaction of high molecular alcohols may be only water (see the reaction equations described below). Thus, unlike the oxo method, the present process may not require high pressures, and may not use harmful substances; consequently, it is possible to lower the cost of safety management of plants and of plant construction, and to reduce the general production cost of high molecular alcohols. In addition, the present process may be a global environment-friendly, clean process because the side product of the present reaction may be only water, which is in contrast to the carbon dioxide produced as a side product in the oxo method.

Overall reaction equations of major synthesis reactions of high molecular alcohols are described below.

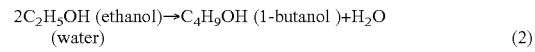

$$2C_2H_5OH \text{ (ethanol)} \rightarrow C_4H_9OH \text{ (1-butanol )}+H_2O \text{ (water)} \quad (2)$$

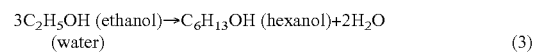

$$3C_2H_5OH \text{ (ethanol)} \rightarrow C_6H_{13}OH \text{ (hexanol)}+2H_2O \text{ (water)} \quad (3)$$

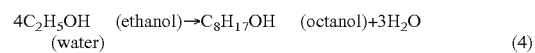

$$4C_2H_5OH \text{ (ethanol)} \rightarrow C_8H_{17}OH \text{ (octanol)}+3H_2O \text{ (water)} \quad (4)$$

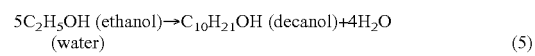

$$5C_2H_5OH \text{ (ethanol)} \rightarrow C_{10}H_{21}OH \text{ (decanol)}+4H_2O \text{ (water)} \quad (5)$$

Based on the ratio of synthesis amounts of these high molecular alcohols, it may be considered that the synthesis reactions of high molecular alcohols from ethanol, catalyzed by calcium phosphate-based catalysts, may be consecutive reactions of ethanol. It may be further considered that high molecular alcohols having an even number of carbon atoms such as butanol having 4 carbon atoms, hexanol having 6 carbon atoms, octanol having 8 carbon atoms and decanol having 10 carbon atoms, may be synthesized from ethanol having 2 carbon atoms. Provided that high molecular alcohols mentioned above may be synthesized as a result of the consecutive reactions of ethanol, the above-mentioned reactions (3) to (5) may be described as the following equations (6) to (8).

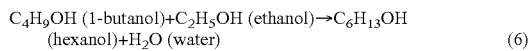

$$C_4H_9OH\ (1\text{-butanol}) + C_2H_5OH\ (\text{ethanol}) \rightarrow C_6H_{13}OH\ (\text{hexanol}) + H_2O\ (\text{water}) \quad (6)$$

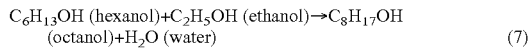

$$C_6H_{13}OH\ (\text{hexanol}) + C_2H_5OH\ (\text{ethanol}) \rightarrow C_8H_{17}OH\ (\text{octanol}) + H_2O\ (\text{water}) \quad (7)$$

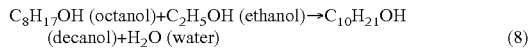

$$C_8H_{17}OH\ (\text{octanol}) + C_2H_5OH\ (\text{ethanol}) \rightarrow C_{10}H_{21}OH\ (\text{decanol}) + H_2O\ (\text{water}) \quad (8)$$

The present inventors have pursued their keen studies for the effect of contact times in ethanol conversion reactions, and as a result, have found that the above-mentioned high molecular alcohols can be synthesized in a highly selective manner by contacting ethanol with a calcium phosphate-based catalyst for a contact time of 0.4 seconds or longer. With regard to the relationship between the contact times and the selectivity of reactants in catalytic reactions, it is common that as the contact time is prolonged, the selectivity of a single substance is decreased because of condensation polymerization of raw materials and multiple reactions. In the process of the present application, however, the selectivity of high molecular alcohols can be improved by prolonging the contact time to 0.4 second or longer at an arbitrary temperature.

With regard to the relationship between the contact times and the abundance ratios of high molecular alcohols, consecutive reactions of ethanol proceeded as the contact time was prolonged, and alcohols with larger molecular weight were synthesized. This is attributed to the fact that these high molecular alcohols are reaction intermediates in ethanol conversion reactions catalyzed by hydroxyapatite catalysts.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawing, in which.

DETAILED DESCRIPTION

Figure 1:
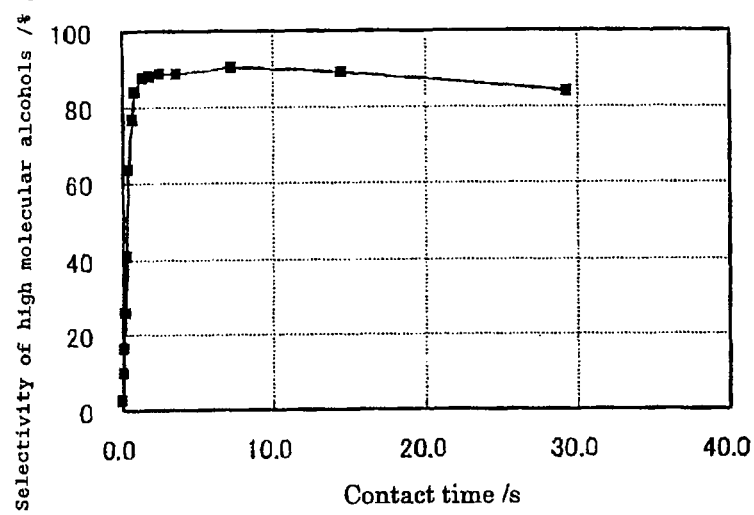
FIG. 1 is a graph showing the relationship between the contact times and the selectivity of high molecular alcohols in Table 1.

As calcium phosphate-based catalysts, the following are known examples: hydroxyapatite $C_{10}(PO_4)_6(OH)_2$, tricalcium phosphate $Ca_3(PO_4)_2$, calcium monohydrogen phosphate $CaHPO_4 \cdot (0{\sim}2)H_2O$, calcium diphosphate $Ca_2P_2O_7$, octacalcium phosphate $Ca_8H_2(PO_4)_6 \cdot 5H_2O$, tetracalcium phosphate $Ca_4(PO_4)_2O$, amorphous calcium phosphate $Ca_3(PO4)_2 \cdot nH_2O$, etc. Though hydroxyapatite is generally indicated by the stoichiometric composition mentioned above, it can form an apatite structure even though it does not meet the stoichiometric composition. Such hydroxyapatite with non-stoichiometric composition can be indicated by $C_{10}-Z(HPO_4)Z(PO_4)_6-Z(OH)_2-Z \cdot nH_2O$ $\{0<Z\leq 1,\ n=0{\sim}2.5\}$. Amorphous calcium phosphate-based catalysts refer to calcium phosphate-based catalysts which show halos in their x-ray diffraction patterns.

The present invention is designed to efficiently produce the high molecular alcohols mentioned above by using these calcium phosphate-based catalysts to optimize the reaction conditions, i.e., the contact time and the reaction temperature.

In the present invention, a method for producing calcium phosphate-based compounds used as catalysts is not particularly limited, and the catalysts can be synthesized by publicly known synthesis methods such as the solid phase reaction (dry method), the precipitation reaction (wet method), the solid phase reaction (wet method), and the hydrothermal synthesis method.

For example, hydroxyapatite is synthesized as follows:
(1) solutions of calcium salt and phosphate salt at prescribed concentrations are added dropwise, while adjusting its pH, to an aqueous solution being stirred;
(2) precipitated products are recovered, washed, dried, ground, and calcinated if necessary, and used as a raw material of catalysts.

The preferred calcium salt is $Ca(OH)_2$ or $Ca(NO_3)_2$, and the preferred phosphate salt is ammonium phosphate salt. The Ca/P molar ratio of hydroxyapatite can be controlled by directing the mixing ratio of salts as raw materials and the synthesis conditions. For instance, when the aqueous solution is adjusted to be basic with ammonia water, etc., at a time of synthesis, the Ca/P molar ratio will be higher, and when the aqueous solution is adjusted to be neutral or weakly acidic with dilute acid, the Ca/P molar ratio will be lower. In addition, hydroxyapatite wherein the Ca/P molar ratio is controlled can be obtained by mixing calcium phosphate-based catalysts with known Ca/P molar ratios and then calcinating them in a water atmosphere.

In case hydroxyapatite is used as a catalyst, the Ca/P molar ratio is adjusted to a range of 1.4 to 1.8, preferably, 1.5 to 1.7, and the calcination temperature and the calcination atmosphere are selected in accordance with the purposes. At that time, it is preferred that the specific surface area of the catalyst is 2 m²/g or larger.

Catalytically, the control of the Ca/P molar ratio in calcium phosphate-based catalysts refers to control of the types and the distribution densities of solid acid sites and solid base sites, which are active sites on the catalyst surface. Here, the intensity and the amount of acid sites and base sites can be assessed by $NH_3$-TPD (Temperature Programmed Desorption) and $CO_2$-TPD, or pyridine adsorption, indicator method, etc. In addition, as for methods for controlling the acidity and the basicity of the catalyst surface, a method to support a metal thereon is generally known.

For example, supporting dehydrogenation reaction accelerating-metals typically including Ni, Zn, Cu, Pd or Pt on hydroxyapatite induces the same effect as an increase in the Ca/P molar ratio, i.e., there is an increase in the solid basicity. Further, regarding hydroxyapatite, supporting dehydration reaction accelerating-metals typically including Al induces the same effect as a decrease in the Ca/P molar ratio, i.e., there is an increase in the solid acidic feature. Therefore, the acidity/basicity of the surface of hydroxyapatite catalysts can be changed also by supporting such metals thereon instead of changing the Ca/P molar ratios. In addition, a plurality of metals can be supported together for the purpose of the synergistic effect or the improvement of durability. Metals to be supported together include, for example, transition metals such as Zn, Co, Cr, Mo, W, Fe, Ni, Cu, Mn, Ti, V, Ga, Zr, Nb, Cd, In, Sn, Sb, Pb, La, Ce, Eu and Y; or noble metals such as Pt, Pd, Rh, Au, Ir, Ru and Ag; and alkali metals or alkali earth metals such as Ba, Na, K, Li, Sr, Ca, Mg, Cs and Rb. In some cases, oxides or sulfides of these metals can also be used. These substances are used in a range of 0.05 to 70 mol % on the basis of calcium in calcium phosphate-based catalysts.

In the present invention, when high molecular alcohols and mixtures thereof are synthesized from ethanol as a raw material, wherein a calcium phosphate-based catalyst is used, control of the acidity and the basicity of the catalyst surface (for instance, the Ca/P molar ratio of the calcium phosphate-based catalyst), and reaction conditions (contact time, reaction temperature, pressure, etc.) are appropriately selected in order to increase the selectivity of desired high molecular alcohols.

The calcium phosphate-based catalysts adjusted as described above can be used in any form, for example, in a form of granules, powders, etc., and also can be used after they are formed into an arbitrary form such as spheres, pellets, honeycombs, as needed, and dried and calcinated. The calcium phosphate-based catalysts can be supported on conventional carriers well known to a person skilled in the art such as alumina, silica, alumina-silica, zeolite, and clay mineral. Calcination is conducted at 200° C. to 1200° C., preferably at 400° C. to 700° C.

The reaction temperature of the present application, suitable for synthesizing high molecular alcohols by contacting ethanol with a calcium phosphate-based catalyst, is usually selected preferably from a range of 150° C. to 450° C., more preferably 200° C. to 350° C. Though there is a means of maintaining the high selectivity of high molecular alcohols even when the temperature is 150° C. or lower, yield is lowered and economic efficiency is worsened due to the low conversion rate of ethanol. Further, in case the temperature is 450° C. or higher, though the conversion rate of ethanol is increased, the selectivity of high molecular alcohols is lowered, unwanted reaction products are increased and there emerge a new problem of disposal of these products. Also, economic efficiency is worsened.

The contact time of the present application is usually 0.4 seconds or longer, preferably 0.6 seconds or longer. When the time is shorter than 0.4 seconds, synthesis yield is lowered and economic efficiency is worsened, due to the low selectivity of high molecular alcohols and the low conversion rate of ethanol. In case the reaction is conducted in a low temperature range, a batch reactor, which is equivalent to infinitely large contact time, can be also used to increase the conversion rate of ethanol. In the reaction conducted in a high temperature range, when the contact time is prolonged, other reactions are increased and the selectivity of high molecular alcohols is decreased.

The reaction to synthesize high molecular alcohols from ethanol is an exothermic reaction. Consequently, when the high yield of high molecular alcohols is set as a target, temperature rise inside a reaction tower, caused by heat of reaction, becomes prominent. As a result, there emerge problems such as a decrease in the selectivity of high molecular alcohols caused by the emergence of other reactions including ethanol decomposition reactions, deterioration of catalysts caused by catalyst temperature rise, and a decrease in the durability of reactors. Therefore, in case of reactions to synthesize high molecular alcohols from ethanol, it is more suitable for industrialization to set high selectivity as a goal than to pursue high yield. However, provided that a system for removing heat of reaction is introduced into a reaction tower, such limitation is not applied.

It is possible to react ethanol efficiently by contacting ethanol with a catalyst directly in the gas phase or in the presence of an inert carrier gas such as nitrogen or helium. At that time, a reactive gas such as hydrogen or hydrocarbon may be added to the carrier gas in order to maintain the catalytic activity.

With regard to reaction forms in a reaction tower, any method such as a batch method, a continuous method, a fixed bed, a moving bed, a fluidized bed or a slurry bed can be used, and the reaction can be conducted at normal pressure or under pressure. In case of high molecular alcohol synthesis reactions, carbons are precipitated on the catalyst surface due to prolonged period of use, and this may result in a decrease in the ethanol conversion rate and changes in the nature of reactions. In such case, a regeneration treatment, wherein a catalyst is heated in oxygen atmosphere, is periodically conducted. The activity of the catalyst can be restored by this treatment. Consequently, in case of reaction conditions under which a lot of carbons are precipitated on catalysts, a plant operated in accordance with the above-mentioned system, in which a catalyst regeneration apparatus is incorporated, is effective.

High molecular alcohols thus obtained can be separated and purified with the use of conventionally used separation and purification methods, for example, rectification, microporous membrane separation, extraction, and adsorption.

The invention will now be further described by way of the following non-limiting examples which further illustrate the invention, and are not intended, nor should they be interpreted to, limit the scope of the invention.

A catalyst was synthesized as follows. With regard to the obtained powder, a powder X-ray diffractometer M18XHF22 manufactured by MacScience was used for the crystal structure, and SA3100 manufactured by COLTER and an X-ray fluorescence spectrometer RIX1000 manufactured by Rigaku Denki Kogyo Co., Ltd. were used for the measurement of the specific surface area and the Ca/P molar ratio, respectively.

EXAMPLES

Example 1

Preparation of Catalyst

A solution prepared by dissolving 225.2 g of calcium nitrate: $Ca(NO_3)_2 \cdot 4H_2O$ in 5.0 liters of distilled water and a solution prepared by dissolving 78.87 g of ammonium phosphate: $(NH_4)_2HPO_4$ in 3.0 liters of distilled water were added dropwise to aqueous ammonia of which pH had been adjusted to 9 to 11 under a nitrogen atmosphere, and the resultant mixture was stirred for one day. Subsequently, the mixture was filtrated, washed with water, and dried to obtain a powder. Ion-exchange water was added to the obtained powder, and the resultant mixture was crushed for 48 hours with a ball mill. The slip thus obtained was matured and dried at 140° C. in an oven. The resultant powder was calcinated in the air at 600° C. for 2 hours to obtain a powdery catalytic composition whose Ca/P molar ratio was 1.64.

Example 2

Evaluation of Catalytic Property

A fixed bed gas flow catalytic reactor was used as a reactor. The powdery catalyst was formed into tablets of 14 to 26 mesh. The tablets were filled in a reaction tube in an amount in accordance with the contact time, and a thermal dehydration treatment was conducted as a pretreatment under carrier gas (1% Ar/He-based; flow 112 ml/min) atmosphere, at 500° C. for 30 minutes. After the pretreatment, the tablets were reacted at normal pressure under the conditions of ethanol concentration of 16 vol %, carrier gas flow 112 ml/min (total flow 134 ml/min).

In case of the high molecular alcohol synthesis experiment, the reaction temperature was fixed at 300° C., and the contact time was in a range of 0.02 to 29.4 seconds. In the optimization experiment of 1-butanol synthesis conditions, the contact time was fixed at 1.0 second, the ethanol concentration was 8.1%, and the reaction temperature was in a range of 150 to 500° C.

A gas chromatography mass spectrometer (GC-MS) was used for the identification of the components of the reaction gas, and a gas chromatography (GC) (detector: FID) was used for the measurement of the ethanol conversion rate and the selectivity of the synthetic gas. At that time, for the purpose of calculating the selectivity of ethanol as a raw material, butanol, hexanol, octanol and decanol, carbon molar response correction factors of 0.70, 0.85, 0.90, 0.93 and 0.94 were used, respectively.

Ethanol conversion rate (%)=(1−number of moles of carbon in 1-ethanol/total number of moles of carbon)×100

Selectivity of 1-butanol (%)=(number of moles of carbon in 1-butanol/total number of moles of carbon)×100

The selectivities of hexanol, octanol and decanol are calculated in a same manner as in the case of 1-butanol.

Selectivity of high molecular alcohols (%)=selectivity of 1-butanol+selectivity of hexanol+selectivity of octanol+selectivity of decanol.

Figure 2:
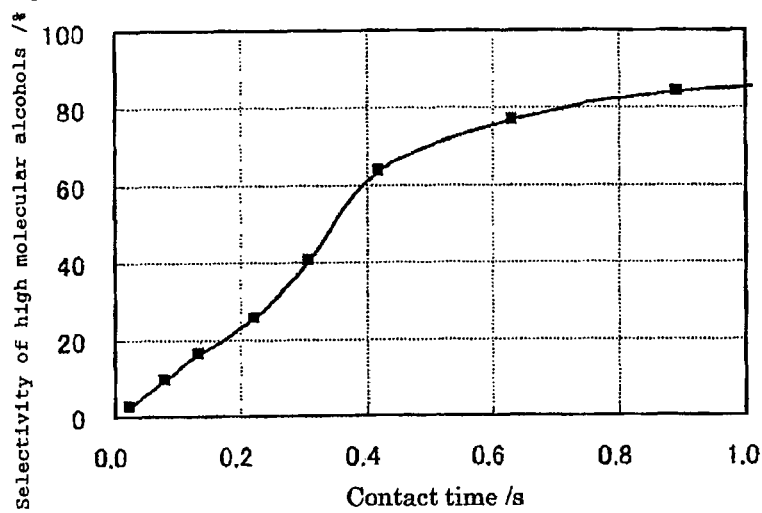
FIG. 2 is a graph in which the part between the contact times of 0.0 and 1.0 second in FIG. 1 is enlarged.

The results of the experiment are shown in Table 1, FIG. 1, and FIG. 2 (an enlarged view of the part between the contact times of 0.0 and 1.0 second in FIG. 1).

TABLE 1

| | Contact time (second) | | | | | | | | | | | | | | |
|---|---|---|---|---|---|---|---|---|---|---|---|---|---|---|---|
| | 0.02 | 0.08 | 0.13 | 0.22 | 0.31 | 0.42 | 0.63 | 0.89 | 1.34 | 1.78 | 2.40 | 3.56 | 7.27 | 14.60 | 29.40 |
| Selectivity of 1-butanol (%) | 2.2 | 7.9 | 12.8 | 22.0 | 35.7 | 58.5 | 70.3 | 77.1 | 79.1 | 77.9 | 75.8 | 72.1 | 64.5 | 55.6 | 45.4 |
| Selectivity of hexanol (%) | 0.3 | 1.5 | 3.3 | 3.5 | 4.5 | 4.9 | 6.0 | 6.4 | 7.3 | 8.6 | 10.7 | 13.4 | 20.2 | 23.8 | 25.2 |
| Selectivity of octanol (%) | 0.0 | 0.1 | 0.2 | 0.2 | 0.3 | 0.3 | 0.4 | 0.5 | 0.8 | 1.1 | 1.8 | 2.4 | 4.0 | 6.9 | 9.5 |
| Selectivity of decanol (%) | 0.0 | 0.0 | 0.0 | 0.0 | 0.0 | 0.0 | 0.1 | 0.1 | 0.2 | 0.2 | 0.3 | 0.5 | 1.3 | 2.4 | 3.9 |
| Selectivity of polymeric alcohols (%) | 2.4 | 9.5 | 16.3 | 25.7 | 40.5 | 63.7 | 76.8 | 84.0 | 87.3 | 87.8 | 88.6 | 88.5 | 90.0 | 88.7 | 84.0 |

Table 1 shows the relationship between the contact times and the selectivity of high molecular alcohols when the ethanol conversion experiment was conducted with the use of a hydroxyapatite catalyst at an ethanol concentration of 16% and at a reaction temperature of 300° C.

The selectivity of 1-butanol reached its maximum value at the contact time of 1.34 seconds, and decreased when the contact time was longer than that. The selectivity of decanol, octanol and hexanol were low, in this order. Up to the contact time of 29.4 seconds, each of selectivity was increased as the contact time was prolonged.

Though the selectivity of high molecular alcohols was very low, 2.4% at the contact time of 0.02 second, it rapidly increased as the contact time was prolonged, and it exceeded 60% at the contact time of 0.4 second. Further, when the contact time was 0.6 second or longer, the selectivity of high molecular alcohols was very high as 70% or more, which is a value advantageous for industrialization.

Example 3

Example of Analysis by Gas Chromatography Mass Spectrometer (GC-MS)

Figure 3:
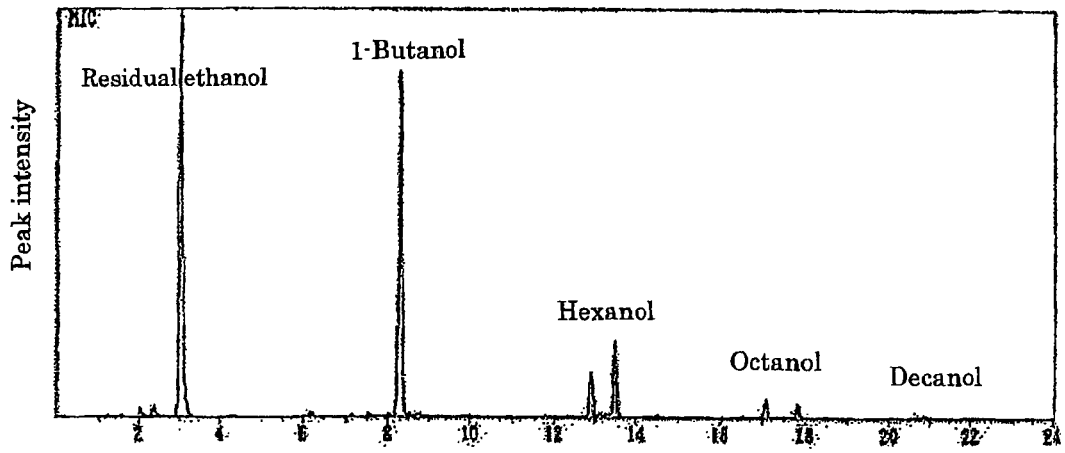
FIG. 3 is a graph showing the analytical results obtained by GC-MS.

The ethanol conversion experiment was conducted with the use of a hydroxyapatite catalyst at an ethanol concentration of 16%, for a contact time of 1.78 seconds and at a reaction temperature of 300° C., and an analysis was conducted with GC-MS. The results are shown in FIG. 3.

The peaks of 1-butanol, hexanol (2 types: iso and normal), octanol (2 types: iso and normal), and decanol (3 types: iso and normal) can be observed at the retention times of 8.5 minutes, 13 to 14 minutes, 17 to 18 minutes, and 20 to 22 minutes, respectively.

It can be seen from this result that high molecular alcohols having 4 or more and an even number of carbon atoms are synthesized selectively.

Example 4

Evaluation of Reaction Temperature and the Selectivity of 1-butanol

Figure 4:
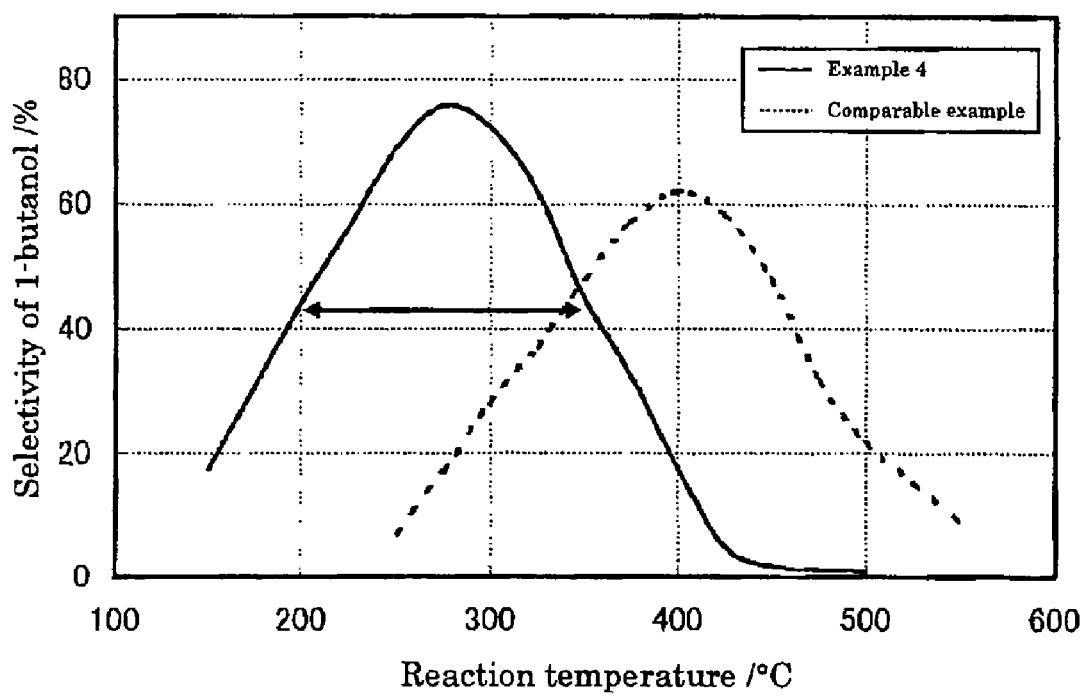
FIG. 4 is a graph showing the relationship between the reaction temperatures and the selectivity of 1-butanol.

The ethanol conversion experiment was conducted with the use of a hydroxyapatite catalyst at an ethanol concentration of 8.1%, for a contact time of 1.0 second. In addition, a same ethanol conversion experiment, except that the contact time was changed to 0.3 second, was conducted for comparison. The results are shown in FIG. 4.

As a result that synthesis properties of 1-butanol at the contact times 1.0 second and 0.3 second were compared, the selectivity of 1-butanol at the contact time of 1.0 second was higher than that of 1-butanol at the contact time of 0.3 second by about 12% at maximum. When the reaction temperatures at the maximum values were compared, the temperature at the contact time of 1.0 second was lower than the temperature at the contact time of 0.3 second by about 75° C.

INDUSTRIAL APPLICABILITY

The catalyst according to the method of the present application can be produced at a low cost and easily, and moreover, is stable to reactions and regeneration treatments. With the catalyst, it is possible to efficiently obtain high molecular alcohols from ethanol by selecting reaction temperatures and contact times.

The high molecular alcohols produced via the present invention has clear industrial applications. For example, butanol can be used as a solvent for a wide variety of chemical and textile processes, in organic synthesis and as a chemical intermediate. It can also be used as a paint thinner and a solvent in other coating applications, as a component in hydraulic and brake fluids, as a base for perfumes, and potentially as a biofuel. Octanol can be used in the manufacture of various esters (both synthetic and naturally occurring), such as octyl acetate, which are used in perfumes and flavors. Finally, decanol can be used in the manufacture of plasticizers, lubricants, surfactants and solvents.

The invention is further described by the following numbered paragraphs:

i. A method for synthesizing a high molecular alcohol having 4 or more and an even number of carbon atoms, wherein ethanol is brought into contact with calcium phosphate for a contact time of 0.4 second or longer.

ii. A method for synthesizing 1-butanol, wherein ethanol is brought into contact with calcium phosphate for a contact time of 0.4 second or longer, and at 200° C. to 350° C.

iii. The method for synthesizing a high molecular alcohol according to paragraph i, wherein the calcium phosphate is hydroxyapatite.

iv. The method for synthesizing 1-butanol according to paragraph ii, wherein the calcium phosphate is hydroxyapatite.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for synthesizing one or more high molecular alcohols having 6 or more and an even number of carbon atoms, comprising contacting ethanol with calcium phosphate for a contact time of 0.6 second or longer.

2. The method for synthesizing one or more high molecular alcohols according to claim 1, wherein the calcium phosphate is hydroxyapatite.

3. The method of claim 1, wherein water is synthesized by the method.

4. The method of claim 2, wherein the ethanol is contacted with the calcium phosphate at 200° C. to 350° C.

5. The method of claim 1, wherein the contact time is 0.63 to 29.40 seconds.

6. The method of claim 5, wherein the one or more high molecular alcohols comprise hexanol, and wherein the selectivity for hexanol is 6.0 to 25.2%.

7. The method of claim 5, wherein the one or more high molecular alcohols comprise octanol, and wherein the selectivity for octanol is 0.4 to 9.5%.

8. The method of claim 5, wherein the one or more high molecular alcohols comprise decanol, and wherein the selectivity for decanol is 0.1 to 3.9%.

9. The method of claim 5, wherein the one or more high molecular alcohols comprise hexanol, octanol, and decanol; and wherein the selectivity for hexanol, octanol, and decanol in combination is 6.5 to 38.6%.

10. The method of claim 5, wherein the one or more high molecular alcohols comprise hexanol, octanol, and decanol; wherein the selectivity for hexanol is 6.0 to 25.2%, the selectivity for octanol is 0.4 to 9.5%, and the selectivity for decanol is 0.1 to 3.9%.

11. The method of claim 1, wherein the ethanol is synthesized by fermentation.

12. A method for synthesizing 1-butanol, comprising contacting ethanol with calcium phosphate for a contact time of 0.6 second or longer, wherein the selectivity for butanol is 70.3% or more.

13. The method of claim 12, wherein the contact time is 0.63 to 3.56 second.

14. The method of claim 13, wherein the selectivity for butanol is 70.3% to 79.1%.

15. The method of claim 12, wherein the calcium phosphate is hydroxyapatite.

16. The method of claim 12, wherein the ethanol is contacted with the calcium phosphate at 200° C. to 350° C.

17. The method of claim 12, wherein the ethanol is synthesized by fermentation.

18. The method of claim 12, wherein the selectivity for butanol is 70.3% to 79.1%.

19. A method for synthesizing 1-butanol at a selectivity of 70.3% or more, comprising contacting ethanol with calcium phosphate for a contact time of 0.6 second or longer, and at 200° C. or more to less than 350° C., wherein the calcium phosphate does not support a metal.

* * * * *